(12) United States Patent
Matsumoto (10) Patent No.: US 8,809,066 B2
(45) Date of Patent: Aug. 19, 2014

(54) APPARATUS AND METHOD FOR IMAGE DETECTION OF TEST STRIP COMPRISING CODE AREA

(75) Inventor: Shigeki Matsumoto, Hyogo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/528,322

(22) Filed: Jun. 20, 2012

(65) Prior Publication Data
US 2012/0329170 A1    Dec. 27, 2012

(30) Foreign Application Priority Data
Jun. 23, 2011   (JP) ................... 2011-139400

(51) Int. Cl.
G01N 21/00    (2006.01)
G01N 21/84    (2006.01)
G01N 33/487   (2006.01)
G01N 21/78    (2006.01)

(52) U.S. Cl.
CPC ...... *G01N 21/8483* (2013.01); *G01N 33/48771* (2013.01); *G01N 21/78* (2013.01)
USPC ............... 436/164; 422/420; 422/425

(58) Field of Classification Search
CPC .............. A61B 2562/0295; G01N 21/848378; G01N 33/48771; G01N 33/54366; G01N 33/48; G01N 33/54393; G01N 35/00; G01N 27/3272
See application file for complete search history.

(56) References Cited

U.S. PATENT DOCUMENTS

| 5,408,535 | A  | * | 4/1995 | Howard et al. ............... 382/128 |
| 7,578,973 | B2 | * | 8/2009 | Call et al. ....................... 422/83 |
| 2005/0074899 | A1 | * | 4/2005 | Polito et al. ................... 436/514 |
| 2005/0161345 | A1 | * | 7/2005 | Groll et al. .................... 205/792 |

FOREIGN PATENT DOCUMENTS

JP    2010-101715 A    5/2010

* cited by examiner

*Primary Examiner* — Yelena G Gakh
(74) *Attorney, Agent, or Firm* — Rader, Fishman & Grauer PLLC (57) ABSTRACT

An analyzing apparatus contains an image detection unit and an analysis unit. The image detection unit contains a view field area that covers at least a reaction area and a background area in a test piece. The reaction area exhibits a reaction color when exposed to a test substance in a specimen. The analysis unit detects the test substance based on the reaction color and determines, during detection of the test substance, whether a state of the background area falls within an acceptable range set for the test substance.

28 Claims, 6 Drawing Sheets

APPARATUS AND METHOD FOR IMAGE DETECTION OF TEST STRIP COMPRISING CODE AREA

CROSS-REFERENCES TO RELATED APPLICATION

This application claims priority from Japanese Patent Application Serial No. 2011-139400 filed Jun. 23, 2011, the contents of which are incorporated herein by reference in its entirety.

BACKGROUND

1. Technical Field

The present invention relates to an analyzing apparatus and an analyzing method for detection or quantitation of a test substance by using a technique such as immunochromatography.

2. Related Art

In recent years, Immunochromatography (immunological chromatography) has been attracting attention as an approach to Point of Care Testing (POCT) carried out at "a place close to a patient" such as a consultation room and ward. The POCT uses an immunochromatography test piece (strip), which enables analysis of a test substance contained in a test fluid, such as blood or urine, through a simple operation like delivery of the test fluid by drops onto the test piece, without adjustment of any reagent. This operation system is very useful to analyze a test substance within a test fluid in a simple and quick manner, and thereby various test pieces are now put into practice.

For example, Japanese Patent Application Publication No. 2010-101715 discusses an analyzing apparatus for such a POCT through Immunochromatography, the apparatus using a test piece having a reaction area that causes a color reaction with a test substance in a specimen. In the apparatus, a light source emits light to illuminate the reaction area, so that the scattering light (or transmitted light or reflected light) from the test piece passes through an appropriate optical light system to an image sensor such as a Charge Coupled Device (CCD) for focusing. The amount of the light obtained at pixels of the image sensor is converted into luminance data for analysis, to quantify the concentration of the test substance in the specimen.

Accordingly, such an analyzing apparatus for a POCT, which uses Immunochromatography, is required to provide highly reliable measurement in a short period of time without complicated operations. Unfortunately, the above analyzing apparatus cannot always provide a reliable measurement (analysis) result. The uncertainty comes from reasons set forth below. For example, when blood is used as a specimen, the red blood cells in the blood sometimes break, releasing protoplasm out of the red blood cells. In this case, the protoplasm flows over the reaction area of a test piece, which is supposed to exhibit a color as a reaction only with a test substance. Consequently, in the resultant image data, the contrast of the image data of the reaction area relative to that of background is likely to be inaccurate, because the color of the reaction area is generated by the reaction with not only the test substance but also the protoplasm. In addition, the blood sometimes contains chyle. In such case, the color of the reaction area is also affected by the chyle. A urine specimen also sometimes contains chyle, resulting in a similar problem to the resultant color and contrast in the case with a blood specimen. As described above, a specimen containing any unintended substance (interfering substance) is highly likely to generate a color at a reaction area that does not reflect the target of a test. In the above analyzing apparatus, however, the concentration of a test substance is possibly quantified based on an inaccurate color, and thereby an incorrect analysis result is output to a user.

SUMMARY OF THE INVENTION

The present invention was made in view of the above situation, and it is an object of the present invention to provide an analyzing apparatus and analyzing method capable of providing highly reliable detection or quantitation of a test substance by using a technique such as Immunochromatography.

An analyzing apparatus according to the present invention includes: an image detection unit that comprises a view field area configured to cover at least a reaction area and a background area in a test piece, the reaction area being configured to exhibit a reaction color when exposed to a predetermined test substance in a specimen; and an analysis unit configured to detect the test substance based on the reaction color. The analysis unit is configured to determine, during detection of the test substance, whether a state of the background area falls within an acceptable range set for the test substance.

In the analyzing apparatus according to the present invention, the test piece may have a code area displaying a code, the code area and the reaction area lying on the same surface of the test piece, the code containing information of the color reaction and information of the acceptable range for the background area, and the image detection unit has an area of a field of view further covering the code area. The analyzing apparatus according to the present invention can be configured to further include a storage unit to record information of the acceptable range for the background area.

An analyzing method according to the present invention includes: obtaining reaction area image data from a reaction area of a test piece, the reaction area being configured to exhibit a reaction color when exposed to a predetermined test substance in a specimen; obtaining background area image data from a background area in the test piece; calculating a concentration of the predetermined test substance, in a concentration calculation process using an analysis unit based on the image data of the reaction area; and determining, during detection of the predetermined test substance, whether a state of the background area falls within an acceptable range set for type of the predetermined test substance, in a determination process based on the image data of the background area obtained by the image detection unit.

In the analyzing method according to the present invention, in the determination process, when it is determined that the state of the background area is out of the acceptable range, an error process may be performed to output an analysis result that includes error message information without the concentration measurement result obtained in the concentration calculation process.

In the analyzing method according to the present invention, preferably, the acceptable range may include a sub-setting for a caution-required range to indicate that a color of the reaction area is unlikely to be a color generated by the predetermined test substance itself, and when it is determined that a state of the background area is within the caution-required range in the acceptable range in the determination process, a caution information adding process is performed to output an analysis result that includes caution message information caveating the concentration measurement result obtained in the concentration calculation process.

In the analyzing method according to the present invention, preferably, the test piece may have a code area displaying a code, the code area and the reaction area lying on the same surface of the test piece, the code encoding information of the color reaction and information of the acceptable range for the background area, and the image detection unit obtains image data of an analyzing area covering the reaction area, the background area, and the code area.

The analyzing method according to the present invention may make it discriminable whether the reaction area of a test piece exhibits a color generated by the test substance itself or a color affected by an interfering substance such as some abnormality of the specimen. As a result, an analysis result reflecting the states of the specimen and the test piece 20 can be obtained.

The analyzing apparatus according to the present invention using the analyzing method may provide a highly reliable analysis result, preventing notification of any incorrect analysis result to a user.

BRIEF DESCRIPTION OF THE DRAWING

Other features and advantages of the present analyzing apparatus and analyzing method will be apparent from the ensuing description, taken in conjunction with the accompanying drawings, in which.

DESCRIPTION

An exemplary embodiment of the present invention is described in detail. An analyzing apparatus according to the present invention is used for quantitative analysis of a test substance contained in a biological sample through a technique such as Immunochromatography. First, description of an immunochromatography test piece used in an analyzing apparatus according to the present invention will be given below.

Figure 1:
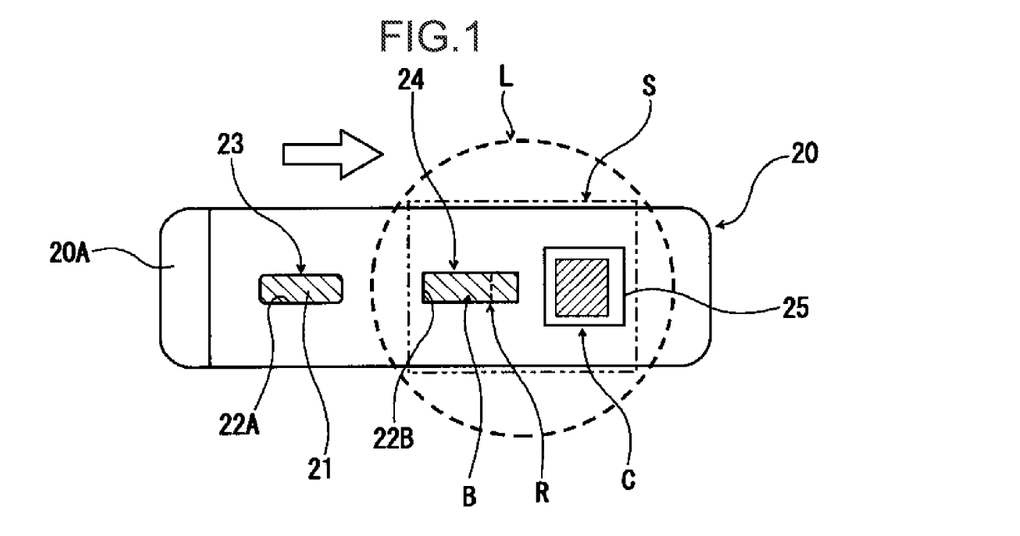
FIG. 1 is a plan view schematically illustrating a structure of an immunochromatography test piece used in an analyzing apparatus according to the present invention.

FIG. 1 is a plan view schematically illustrating a structure of an immunochromatography test piece used in an analyzing apparatus according to the present invention. An immunochromatography test piece 20 (hereinafter, simply referred to as a test piece) includes a case 20A which holds therein a porous carrier 21 such as a filter paper (i.e., which is shown with diagonal lines in FIG. 1), the case having openings 22A and 22B that individually expose the porous carrier 21 to the outside and are positioned apart from each other in the direction a specimen spreads after being deposited in opening 22A (a direction shown by an open arrow in FIG. 1) (hereinafter the "spreading direction"). The opening 22A provides a specimen depositing port 23, and the opening 22B provides a reading port 24. As to the reading port 24, on a surface area of the porous carrier 21, which is exposed to the outside through the other opening 22B of the case 20A, a labeled antibody, and an antibody or antigen corresponding to the test substance are fixed in an area in the shape of a line in a direction (upward and downward in FIG. 1) orthogonal to the spreading direction, so that a reaction area R is formed.

The test piece 20 further includes a two-dimensional code 25 such as a Quick Response code) (hereinafter "QR code" (registered trademark)), at a position of a downstream side of the reading unit 24 in the spreading direction, whereby the code 25 forms a code area C. Accordingly, the test piece 20 includes the reaction area R and the code area C on the same surface thereof. The two-dimensional code 25 can encode basic information of the test piece 20 such as analysis items, its expiration date, and its rot number, and information about the color reaction unique to the test piece 20 such as its reaction time, its calibration curves, and acceptable ranges as criteria to determine a state of a later-described background area B.

Analyzing Apparatus

An analyzing apparatus according to the present invention includes: a detection unit having an image pickup section whose area of a field of view S at least covers an analyzing area including the reaction area R and the background area B which does not include the reaction area R of the test piece 20, the background area being a surface area of the porous carrier 21 exposed outside through the opening 22B, and a control unit having an analysis section to detect a predetermined test substance based on a color level of the reaction area R of the test piece 20.

Figure 2:
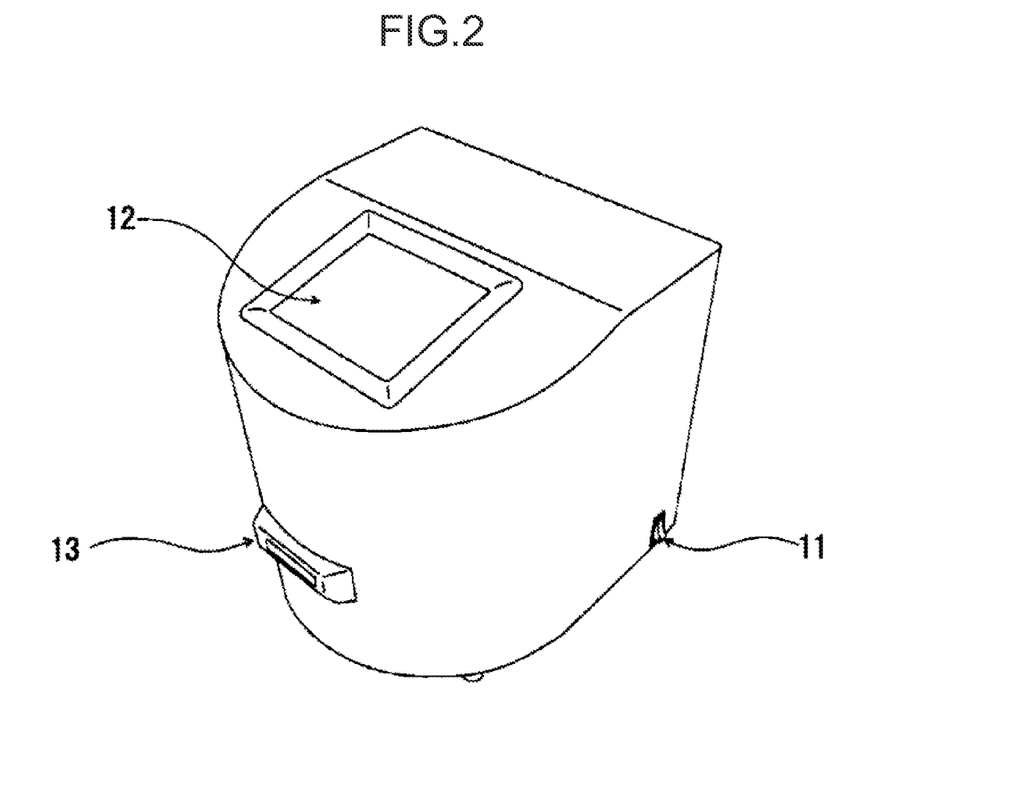
FIG. 2 is a perspective view illustrating an appearance of an analyzing apparatus according to the present invention.
Figure 3:
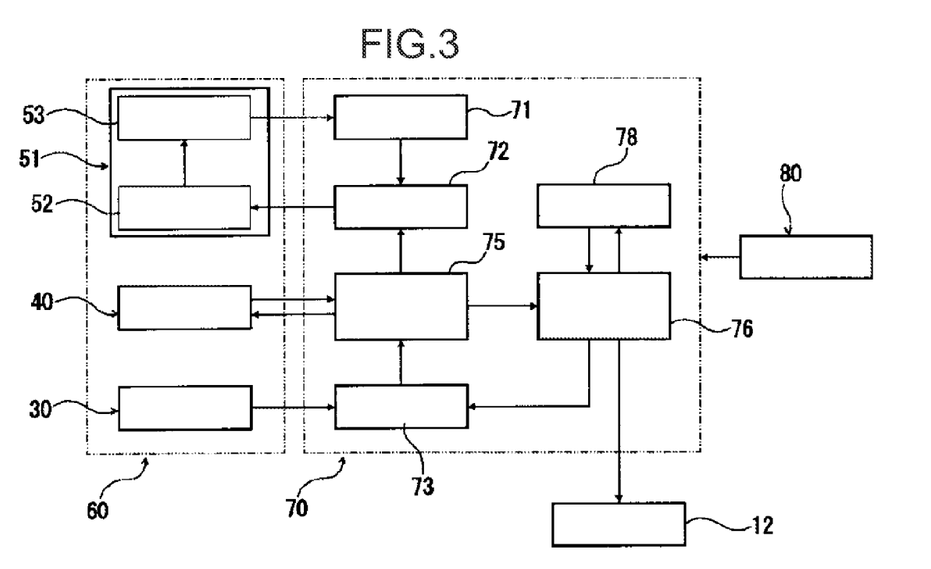
FIG. 3 is a block view schematically illustrating a structure of the analyzing apparatus in FIG. 2.
Figure 4:
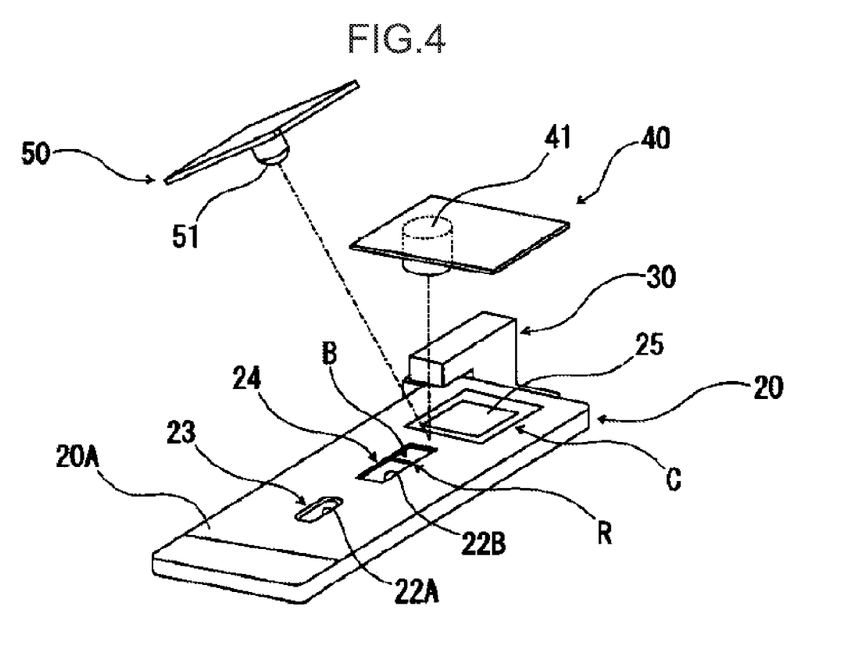
FIG. 4 is a perspective view schematically illustrating a detection unit of the analyzing apparatus in FIG. 2.

FIG. 2 is a perspective view illustrating an appearance of an analyzing apparatus according to the present invention. FIG. 3 is a block view schematically illustrating a structure of the analyzing apparatus in FIG. 2. FIG. 4 is a perspective view schematically illustrating a structure of the detection unit of the analyzing apparatus in FIG. 2. In FIG. 2, the analyzing apparatus includes a power switch 11, a touch panel 12 serving as an operation means to accept ID information of an analyzing specimen and operation command signals and as a display means to display analysis results. The analyzing apparatus further includes a test piece inlet port 13 into which the test piece 20 of the above configuration is horizontally inserted with the surface having the reaction area R and the code area C facing upward.

The analyzing apparatus of the present exemplary embodiment includes a detection unit 60 including: a test piece detection section to detect the presence/absence of the test piece 20; an image detection section having an area of a field of view S that covers an analyzing area including the reaction area R and the code area C of the test piece 20 when the test piece 20 is set at an appropriate position; and an illumination section to illuminate an area L covering the area of the field of view S of the test piece 20 of the image pickup section (i.e., the area to be illuminated, and surrounded by the dashed line in FIG. 1).

The test piece detection section comprises a test-piece detecting sensor 30 such as a photo interrupter.

The image pickup section comprises an image sensor 40 having image capturing elements to receive light, for example, reflected from the test piece 20, and to pick up an image of the light intensity distribution over the analyzing area of the test piece 20. The image sensor 40 can be preferably a device provided with a Complementary Metal-Oxide Semiconductor (CMOS) image sensor 41 having image capturing elements. The image sensor 40 having the CMOS image sensor 41 is capable of suppressing a noise, which is called "smear" arising in a CCD image sensor and caused by overflow of the charge inside the image capturing elements, so that an output of the pixels corresponding to the reaction area R may not be adversely affected.

The illumination section comprises an illumination device including a light source for emitting a color light beam to illuminate the reaction area R of the test piece 20 to provide a high contrast to the color density of the reaction area R. The light source is, for example, a light emitting diode (LED), a semiconductor laser, or a combination of a lamp and a band pass filter. The light source, however, can be preferably an LED emitting a green light beam having a peak wavelength at around 525 nm, because the test piece 20 using, for example, a gold colloid label is colored, for example, pink depending on a test substance. The analyzing apparatus of the present exemplary embodiment includes the illumination device 50 that is provided with, as a light source, an LED 51 having a light emitting element 52 and a light-sensitive element 53 to receive part of radiation from the light emitting element 52 for monitoring. The LED 51 is controlled by Auto Power Control (APC) to suppress variation in light quantity due to disturbances such as ambient temperature, so that a constant amount of light is consistently emitted for illumination. The area L illuminated by the illumination device 50 can be adjusted by, for example, the arrangement position (separation distance) of the illumination device 50 with respect to the surface of the test piece 20.

A control unit 70 includes: a signal amplification section 71 to amplify an output signal which corresponds to an amount of light radiated by the light emitting element 52 and detected by the light-sensitive element 53 of the LED 51 in the illumination device 50; an electric current control section 72 to regulate, through feedback control, an amount of the light output from the LED 51 by adjusting an electric current supplied to the light emitting element 52 such that the signals output from the light-sensitive element 53 after the amplification by the signal amplification section 71 are regulated; a timing section 73 to measure an elapsed time from detection of the test piece 20 by the test-piece detection sensor 30; an image pickup apparatus control section 75 to control operations of the image sensor 40; an analysis section 76 to analyze the image data obtained by the image sensor 40 and calculate a concentration of a test substance in a specimen; and a data storage section 78 to record information contained in the two-dimensional code 25 of the test piece 20 in a rewritable manner.

The image pickup apparatus control section 75 has, for example, a function to adjust image pickup conditions used by the image sensor 40, such that two image data for the analyzing area of the test piece 20 can be obtained respectively under a first image pickup condition and a second image pickup condition different from the first one. The adjustment of the image pickup conditions used by the image sensor 40 can be preferably achieved through an approach in which an exposure time is adjusted by controlling a shutter speed (shutter time) of an electronic shutter of the CMOS image sensor 41 in the image sensor 40 to adjust an amount of exposure (the light quantity received by the CMOS image sensor 41), or an approach in which an amount of exposure is adjusted by controlling an amount of light emitted by the LED 51 of the illumination device 50. The amount of exposure can also by adjusted through adjustment of the gain (sensitivity) or aperture of the CMOS image sensor 41, but it is preferable to adjust the image pickup conditions through control of a shutter speed (shutter time) of an electronic shutter of the CMOS image sensor 41 because a larger amount of exposure based on a larger gain of the CMOS image sensor 41 increases noise and any change in the aperture results in a change of an image picked up.

The first image pickup condition used by the image sensor 40 is set such that an image of the code area C in the analyzing area of the test piece 20 can be picked up at optimal brightness. More specifically, the shutter speed (exposure time) of the CMOS image sensor 41 and/or the light quantity of the LED 51 in the illumination device 50, that is, an amount of exposure to the CMOS image sensor 41 are set such that no point around the two-dimensional code 25 has brightness greater than that of the highest gray level of the CMOS image sensor 41.

The second image pickup condition used by the image sensor 40 is set such that an image of the reaction area R in the analyzing area of the test piece 20 can be picked up at optimal brightness. More specifically, an amount of exposure is set to exceed the amount in the first image pickup condition, and also a shutter speed (exposure time) of the electronic shutter in the CMOS image sensor 41 and/or a amount of the light emitted from the LED 51 in the illumination device 50 are set to exceed those in the first image pickup condition as far as no point in the analyzing area except the reaction area R (i.e., the detecting lines and control lines) has brightness greater than that of the highest gray level of the CMOS image sensor 41. For example, an amount of exposure to the CMOS image sensor 41 in the second image pickup condition can be 1.3 times greater than that in the first image pickup condition.

In the above exemplary embodiment, a shutter speed (exposure time) of the electronic shutter in the CMOS image sensor 41 can be adjusted, for example by changing the operation conditions of CMOS camera modules. An amount of the light emitted from the LED 51 can be adjusted, for example by changing an amount of the electric current supplied to the LED 51.

The analysis section 76 performs the following functions: a process to read information unique to the test piece 20, the information being encoded in the two-dimensional code 25, based on image data of the analyzing area of the test piece 20 captured under the first image pickup condition (hereinafter referred to as "code-reading image data"); and a density calculation process to calculate an optical density of the color of the reaction area R based on image data of the analyzing area captured under the second image pickup condition (hereinafter, referred to as "test substance detecting image data"). Both of the code-reading image data and the test substance detecting image data are expressed in 256 (from 0 to 255) gray levels. For example, when the highest gray levels of the reaction area R and the code area C fall within a range from 200 to 250 gray levels, the information displayed in the code area C and the color exhibited in the reaction area R can be appropriately read.

Thus, in the above analyzing apparatus, the analysis section 76 in the control unit 70 has a function to determine, in detection of a test substance, whether a state of the background area B on the test piece 20 falls within an acceptable range that is set for various types of test substances, based on the image data of the background area B in the test substance detecting image data. More specifically, the analysis section 76 calculates a pixel value of the background area B in the test substance detecting image data, and determines whether the obtained pixel value lies within an acceptable range for the pixel value to be displayed on the touch panel 12. The pixel values can be evaluated based on criteria consisted of: the acceptable range for pixel values; an acceptable range for normal pixel values in cases where undesired substances are included in a specimen; and an acceptable range (attention-required range) for attention-required pixel values in cases where attention is required, for example, when a specimen contains no undesired substance but the color of the reaction area R is unlikely to be the color generated by the test substance itself. The acceptable range for pixel values, the acceptable range for normal pixel values, and the acceptable range for attention-required pixel values can be individually set experimentally or empirically.

Figure 5:
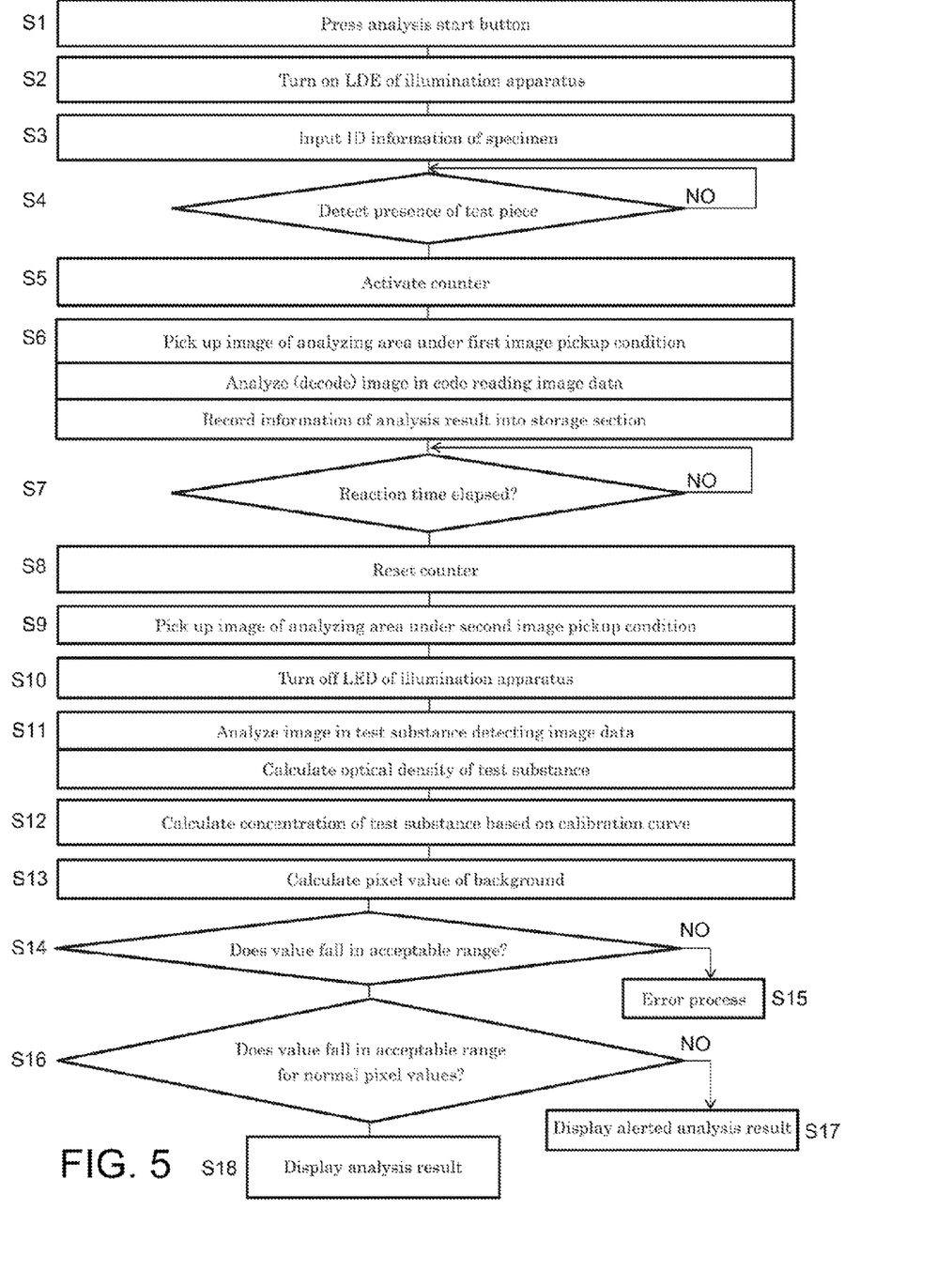
FIG. 5 is a flowchart illustrating an operation performed by the analyzing apparatus in FIG. 2.

An operation of the analyzing apparatus will be described below. When the power switch 11 of the analyzing apparatus is turned on, the touch panel 12 displays a menu screen, which enables the analyzing apparatus to start measuring. As illustrated in FIG. 5, in step S1, by pressing the analysis start button on the touch panel 12, a power feeding device 80, which starts power feed to the control unit 70, is activated. In step S2, the current control section 72 controls and feeds an electric current to the light emitting element 52 to turn on the LED 51. The control of the current fed to the light emitting element 52 is specifically achieved as set forth below. The light-sensitive element 53, which receives light emitted from the light emitting element 52, outputs an electric signal in response to the intensity of the received light. The signal is amplified by the signal amplification section 71, and is input to the current control section 72. The current control section 72 then controls the size of the electric current to be fed to the light emitting element 52 so that the electric signals input to the current control section 72 are regulated.

In step S3, after the touch panel 12 is operated to input ID information of a specimen to be analyzed, the specimen is deposited into a specimen depositing port 23 of the test piece 20, and the test piece 20 is then inserted into the test piece insertion portion 13. In step S4, the test-piece detection sensor 30 in the detection unit 60 detects the presence of the set test piece 20 therein. In step S5, the test-piece detection sensor 30 outputs a test piece detection signal, which activates the timing section 73 to start counting (i.e., a timer starts counting). The timing section 73 outputs an operation command signal to the image pickup apparatus control section 75.

In step S6, the image pickup apparatus control section 75 adjusts the image pickup condition used by the image sensor 40 to the first image pickup condition for the image sensor 40, and the image sensor 40 picks up an image of the analyzing area of the test piece 20 to obtain code detection image data. The analysis section 76 appropriately analyzes an image of the code area C in the code detection image data. The analysis section 76 reads out the information unique to the test piece 20 contained in the two-dimensional code 25, such as information of a reaction time when the color of the reaction area R becomes detectable, information of a calibration curve to calculate the concentration of a test substance contained in the specimen, and criteria information used in a process to determine the state of the background area B, the criteria information containing the acceptable range for pixel values, the acceptable range for normal pixel values, and the acceptable range for attention-required pixel values for the background area B. Among the above information, the calibration curve information and the criteria information are recorded into the data storage section 78. The reaction time in the reaction time information is set into the timing section 73.

In step S7, when the timing section 73 detects that the time elapsed from the detection of the presence of the test piece 20 exceeds the reaction time in the obtained reaction time information, in step S8, the count is reset (i.e., the timer is reset). In step S9, the image pickup apparatus control section 75 adjusts the image pickup condition used by the image sensor 40 to the second image pickup condition for the image sensor 40, and the image sensor 40 picks up an image of the analyzing area of the test piece 20 to acquire test substance detecting image data. After the test substance detecting image data is obtained, in step S10, the image pickup apparatus control section 75 outputs an operation command signal to the current control section 72, which stops current feeding to the light emitting element 52 to turn off the LED 51.

Figure 6:
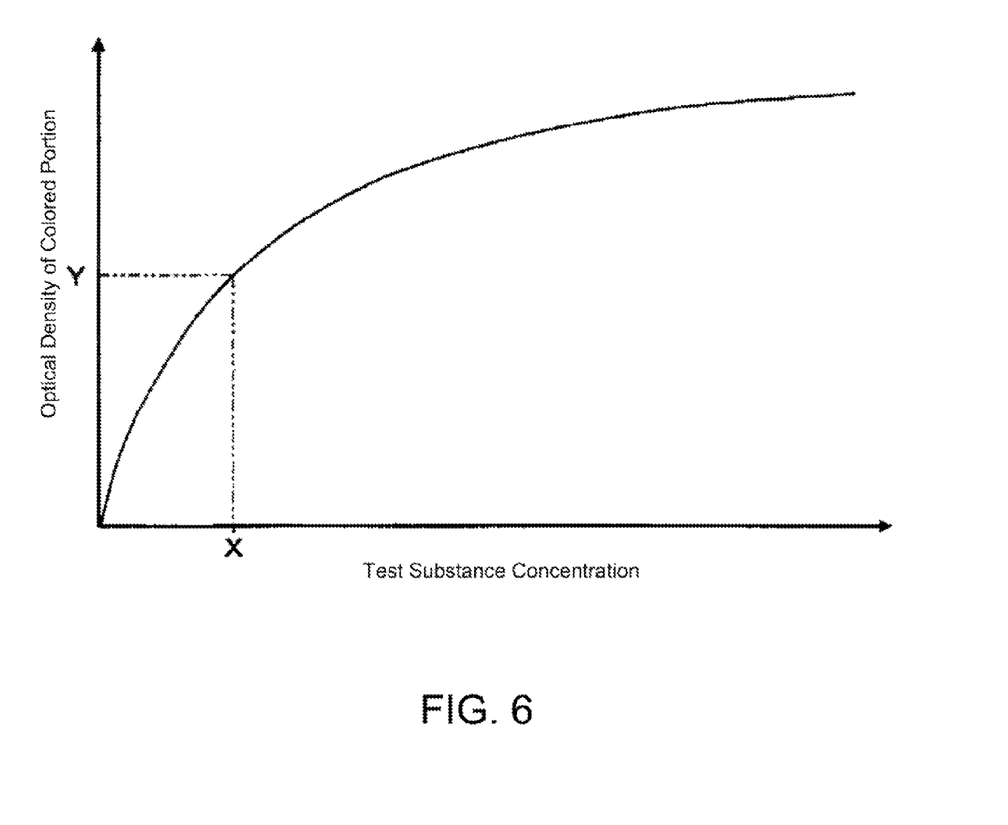
FIG. 6 illustrates a calibration curve indicating the relationship between a test substance concentration and a color optical density.

In step S11, the analysis section 76 appropriately analyzes an image of the reaction area R in the test substance detecting image data, to calculate the optical density of the color exhibited in a line shape in the reaction area R. In step S12, as illustrated in FIG. 6, a concentration calculation process is performed to calculate the concentration X of the test substance corresponding to the calculated optical density Y of the color of the reaction area R, based on the calibration curve according to the calibration curve information obtained by the code-reading image data.

After the calculation of the optical density Y of the color of the reaction area R, the analysis section 76 performs a process to determine the state of the background area B of the test piece 20, based on the image data of the background area B in the test substance detecting image data.

In the determination process, in step S13, the analysis section 76 appropriately analyzes an image of the background area B in the test substance detecting image data, to calculate the optical density of the background area B as a pixel value (hereinafter, referred to as background value). The background value (BG) can be expressed by an equation: $BG=(BG_R+BG_L)/2$, wherein $BG_R$ is a pixel value obtained from pixels located adjacent to the reaction area R in the spreading direction (i.e., the pixel value for the background area B close to the downstream side of the reaction area R), and $BG_L$ is a pixel value obtained from the pixels located adjacent to the reaction area R in a direction opposite to the spreading direction (i.e., the pixel value for the background area B close to the upstream side of the reaction area R).

In the present exemplary embodiment, as the criteria to determine the state of the background area B, three ranges are set: (1) an acceptable range for pixel values, (2) a normal pixel value range, and (3) an attention-required range. The normal pixel value range corresponds to the cases where the reaction area R can be determined to exhibit a color generated by the predetermined test substance itself. The attention-required range corresponds to the cases where the reaction area R cannot be determined to exhibit a color generated by the predetermined test substance itself. Pixel values in the attention-required range (attention-required pixel values) are outside of the normal pixel value range, but the two ranges are both within the acceptable range for pixel values in which an analysis result of the concentration measurement result obtained by the concentration calculation process is to be displayed. In step S14, the acceptable pixel values corresponding to the target test substance in the criteria information are read from the data storage section 78 as background criteria, and a first determination process is performed to determine whether the calculated background value BG falls within the acceptable ranges of the background criteria values.

In step S15, in the first determination process, when the background value BG is found to be out of the acceptable range for the background criteria values, an error display process is perform to display an analysis result on the touch panel 12 that includes error message information but does not include the concentration measurement result calculated in the concentration calculation process (step S12). In step S16, when the background value BG is found to be within the acceptable range for background criteria values, a second determination process is performed.

In the second determination process, the normal pixel value range (or the attention-required range), that are set within the range for the acceptable pixel values, corresponding to the target test substance in the criteria information are read from the data storage section 78 as background criteria values, and it is determined whether the calculated background value BG lies within the acceptable ranges for the read background criteria values. In the second determination process, in step S17, when the calculated background value BG is found to be out of the normal pixel value range as background criteria values (and thus to be within the attention-required range), a caution information display process is perform to display an analysis result on the touch panel 12 that includes caution message information caveating the concentration measurement result calculated in the concentration calculation process (step S12). In step S18, when the calculated background value BG is found to be within the normal pixel value range as background criteria values (and thus to be without the attention-required range), the concentration measurement result calculated in the concentration calculation process (step S12) is displayed without a caveat as an analysis result on the touch panel 12.

Figure 7:
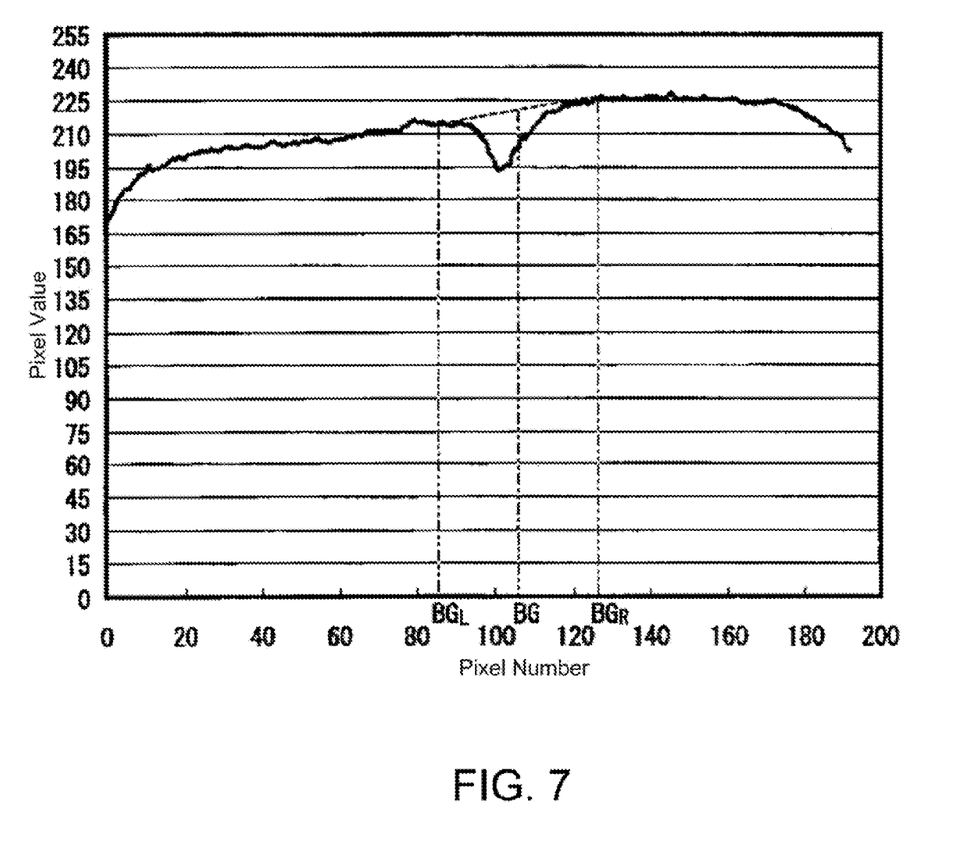
FIG. 7 is a graph illustrating a luminance profile of a specimen in its spreading direction in image data that is captured under a second image pickup condition.
Figure 8:
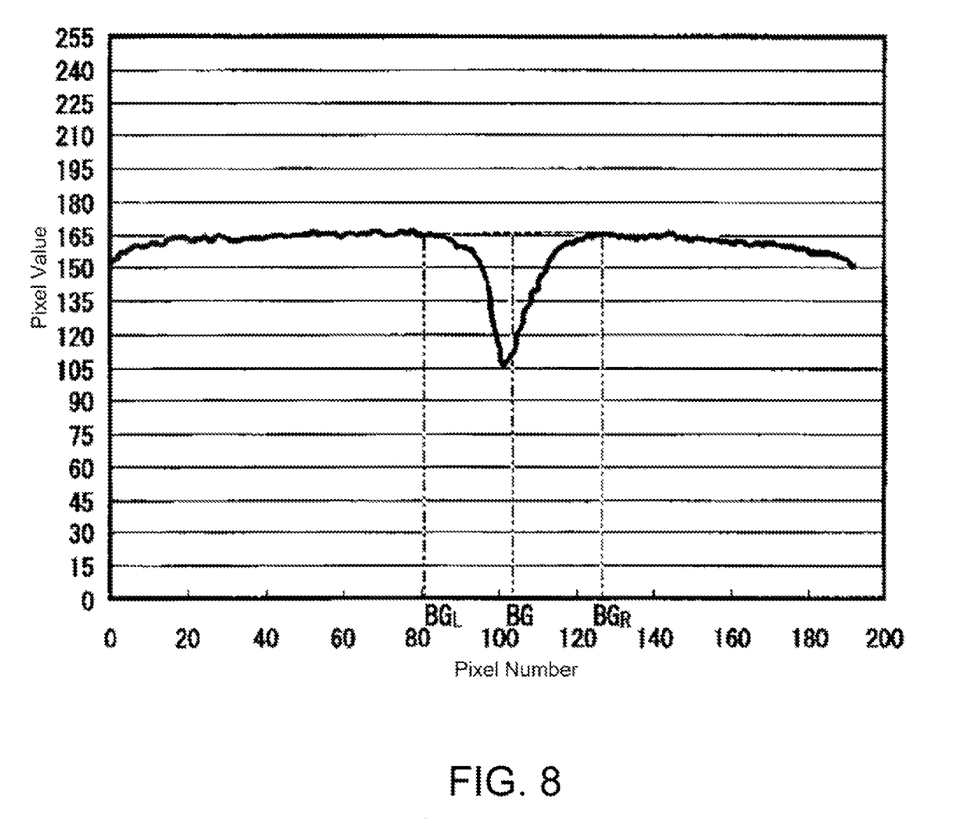
FIG. 8 is another graph illustrating a luminance profile of a specimen in its spreading direction in image data that is captured under a second image pickup condition.

For example, in the case where a predetermined test substance in blood as a specimen is detected, and the background criteria values for the test substance are set to range from above 180 to less than 240 as acceptable range for pixel values, to range from above 200 to less than 240 as a normal pixel value range, and to range from above 180 to less than 200 as an attention-required range, when luminance profiles, in the spreading direction, of the reaction area R and the background area B in the direction in the test substance detecting image data are obtained as illustrated in FIG. 7 for example, the resultant background value BG is 218.8, and thereby in the second determination process, the reaction area R is determined to exhibit a color generated by the test substance itself because the background value BG is in the normal pixel value range. In other words, the specimen is determined to be normal, and the concentration measurement result is displayed without caveat as an analysis result on the touch panel 12. In contrast, when luminance profiles, in the spreading direction, of the reaction area R and the background area B in the test substance detecting image data are obtained as illustrated in FIG. 8 for example (based on the same pixels as those in FIG. 7), the resultant background value BG is 165.4, and thereby in the first determination process, it is determined that the color of the reaction area R is unlikely to be the one of the test substance itself because the background value BG falls outside of the acceptable range for pixel values, and an error process is performed. Especially, when the background value BG is less than the lower limit of the acceptable range values (i.e., equal to or less than 180 in this example), it is determined that something abnormal happened to the specimen itself, such as release of hemoglobin due to lysis of red blood cells in the blood (hemolyzed specimen). When the background value BG is equal to or greater than the upper limit of the acceptable range values (i.e., equal to or greater than 240 in this example), it is determined that the specimen has not been deposited by drops yet or that the drops are insufficient.

Thus, according to the above analyzing method, the analysis section 76 performs a determination process about a state of the background area B of the test piece 20 based on the image data of the background area B in the test substance detecting image data, which makes it discriminable whether the reaction area R exhibits a color generated by the test substance itself or a color affected by an interfering substance such as some abnormality of the specimen. As a result, an analysis result reflecting the states of the specimen and the test piece 20 can be obtained. The analyzing apparatus that utilizes this analyzing method provides a highly reliable analysis result as described above, preventing notification of any incorrect analysis result to a user.

While the exemplary embodiment of the present invention has been described, the present invention is not limited to the above exemplary embodiment, and various changes can be made. For example, the background criteria values need not to be contained in the code of a test piece, and may be recorded in the data storage section of the control unit. In the analyzing apparatus of the above exemplary embodiment, the image pickup apparatus is configured to have the area of the field of view covering both of the reaction area and the code area of a test piece, but the image pickup apparatus may be configured to obtain image data of the reaction area and the background area and image data of the code area in series, by moving one of the image pickup apparatus and the test piece relative to the other. In addition, the image pickup condition needs not to be necessarily changed to obtain the test substance detecting image data and the code-reading image data. The test substance detecting image data and the code-reading image data can be obtained under the same image pickup condition. The reaction area and the background area, however, get dark as a specimen is delivered and spreads, and therefore, it is desirable to change the image pickup condition for obtaining each set of data. Furthermore, specific configurations such as the positioning and posture of the illumination device in the detection unit, and the positioning and posture of the image pickup apparatus can be properly changed as needed.

The preceding description has been presented only to illustrate and describe exemplary embodiments of the present analyzing apparatus and analyzing method. It is not intended to be exhaustive or to limit the invention to any precise form disclosed. It will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, it is intended that the invention not be limited to the particular embodiment disclosed as the best mode contemplated for carrying out this invention, but that the invention will include all embodiments falling within the scope of the claims. The invention may be practiced otherwise than is specifically explained and illustrated without departing from its spirit or scope.

What is claimed is:

1. An analyzing apparatus, comprising:
   an image detection unit that images a reaction area, a background area, and a code area in a test piece, the reaction area being configured to exhibit a reaction color when exposed to a predetermined test substance in a specimen and the code area displaying a code that encodes information specifying the reaction color and an acceptable pixel value range for the background area; and
   an analysis unit that:
      detects the code in the image of the code area,
      decodes the code,
      detects the presence of the test substance in the specimen by determining a reaction area optical density from the image of the reaction area and comparing the reaction area optical density to calibration information corresponding to the reaction color, and determines a background area optical density from the image of the background area and determines whether the background area optical density falls within the acceptable pixel value range for the background area.

2. The analyzing apparatus of claim 1, wherein detecting the presence of the test substance in the specimen includes calculating a concentration of the test substance in the specimen.

3. The analyzing apparatus of claim 2, further comprising:

a display unit configured to display analysis results, wherein the analysis results include the calculated concentration of the test substance when the analysis unit determines that the background area optical density falls within the acceptable pixel value range for the background area, and include an error message that does not include the calculated concentration of the test substance when the analysis unit determines that the background area optical density does not fall within the acceptable pixel value range for the background area.

4. The analyzing apparatus of claim 3, wherein the code also encodes information specifying a normal pixel value range for the background area that is within the acceptable pixel value range for the background area, the analysis unit determines whether the background area optical density falls within the normal pixel value range for the background area, and the analysis results include a warning indicator along with the determined concentration when the analysis unit determines that the background area optical density falls within the acceptable pixel value range for the background area but not within the normal pixel value range for the background area.

5. The analyzing apparatus of claim 1, wherein the code also encodes information about the test piece, including a reaction time of the test substance in the reaction area.

6. The analyzing apparatus of claim 5, further comprising:

a test piece detection unit that detects the presence of the test piece within the analyzing apparatus, wherein the image detection unit images the code area, detects the code in the image of the code area, and decodes the code after detection of the presence of the test piece and before imaging the reaction area and the background area, with a delay time between the detection of the presence of the test piece and the imaging of the reaction area and the background area being set to exceed the reaction time.

7. The analyzing apparatus of claim 1, further comprising:

a test piece receptacle configured to receive the test piece such that at least the reaction area, the background area, and the code area of the test piece are within a view field area of the image detection unit.

8. The analyzing apparatus of claim 1, wherein the image detection unit images the code area of the test piece under first imaging conditions that are set so as to yield a total exposure in which a brightest region of the code area does not exceed a highest pixel value of the image detection unit, and the image detection unit images the reaction area and the background area of the test piece under second imaging conditions that are set so as to yield a total exposure greater than that of the first imaging conditions.

9. The analyzing apparatus of claim 8, further comprising:

a light source that illuminates the test piece during imaging, wherein the second imaging conditions differ from the first imaging conditions in an amount of light emitted by the light source.

10. The analyzing apparatus of claim 8, wherein the second imaging conditions differ from the first imaging conditions in an exposure time of an image sensor of the image detection unit.

11. The analyzing apparatus of claim 1, wherein the analysis unit outputs an error message when it is determined that the background area optical density does not fall within the acceptable pixel value range for the background area.

12. The analyzing apparatus of claim 11, wherein the code also encodes information specifying a normal pixel value range for the background area that is within the acceptable pixel value range for the background area, the analysis unit determines whether the background area optical density falls within the normal pixel value range for the background area, and outputs a warning indicator but not the error message when it is determined that the background area optical density falls within the acceptable pixel value range for the background area but not within the normal pixel value range for the background area.

13. A method of detecting a test substance in a specimen applied to a test piece that includes a reaction area, a background area, and a code area, the reaction area being configured to exhibit a reaction color when exposed to the test substance and the code area displaying a code that encodes information specifying the reaction color and an acceptable pixel value range for the background area, the method comprising:

imaging the code area, detecting the code in the code area, and decoding the code;

imaging the reaction area and the background area;

detecting the presence of the test substance in the specimen by determining a reaction area optical density from the image of the reaction area and comparing the reaction area optical density to calibration information corresponding to the reaction color; and determining a background area optical density from the image of the background area and determining whether the background area optical density falls within the acceptable pixel value range for the background area.

14. The method of claim 13, wherein detecting the presence of the test substance in the specimen includes determining a concentration of the test substance in the specimen.

15. The method of claim 14, further comprising:

displaying the determined concentration when it is determined that the background area optical density falls within the acceptable pixel value range for the background area and displaying an error message but not the determined concentration when it is determined that the background area optical density does not fall within the acceptable pixel value range for the background area.

16. The method of claim 15, wherein the code also encodes information specifying a normal pixel value range for the background area that is within the acceptable pixel value range for the background area, the method further comprising:

determining whether the background area optical density falls within the normal pixel value range for the background area, and displaying a warning indicator along with the determined concentration when it is determined that the background area optical density falls within the acceptable pixel value range for the background area but not within the normal pixel value range for the background area.

17. The method of claim 13,
wherein the code also encodes information about the test piece, including a reaction time of the test substance in the reaction area, and
the imaging the code area, the detecting the code in the image of the code area, and the decoding the code are performed after the test piece is inserted into an analyzing apparatus and before the imaging the reaction area and the background area, with a delay time between the test piece being inserted into the analyzing apparatus and the imaging the reaction area and the background area exceeding the reaction time.

18. The method of claim 13,
wherein the imaging the code area of the test piece is performed under first imaging conditions that yield a total exposure in which a brightest region of the code area does not exceed a highest pixel value of the image detection unit, and
the imaging the reaction area and the background area of the test piece is performed under second imaging conditions that yield a total exposure greater than that of the first imaging conditions.

19. The method of claim 18,
wherein the second imaging conditions differ from the first imaging conditions in an amount of light emitted by a light source.

20. The method of claim 18,
wherein the second imaging conditions differ from the first imaging conditions in an exposure time of an image sensor used to perform the imaging.

21. The method of claim 13, further comprising:
outputting an error message when it is determined that the background area optical density does not fall within the acceptable pixel value range for the background area.

22. The method of claim 21,
wherein the code also encodes information specifying a normal pixel value range for the background area that is within the acceptable pixel value range for the background area, and the method further comprises:
determining whether the background area optical density falls within the normal pixel value range for the background area, and
outputting a warning indicator but not the error message when it is determined that the pixel value of the background area optical density falls within the acceptable pixel value range for the background area but not within the normal pixel value range for the background area.

23. A method of using the analyzing apparatus of to claim 1, comprising:
causing the image detection unit to image the code area;
causing the analysis unit to detect the code in the code area and decode the code;
causing the image detection unit to image the reaction area and the background area;
causing the analysis unit to detect the presence of the test substance in the specimen by determining a reaction area optical density from the image of the reaction area and comparing the reaction area optical density to calibration information corresponding to the reaction color; and
causing the analysis unit to determine a background area optical density from the image of the background area and determine whether the background area optical density falls within the acceptable pixel value range for the background area.

24. The method of claim 23, further comprising:
causing the analysis unit output an error message when it is determined that the background area optical density does not fall within the acceptable pixel value range for the background area.

25. The method of claim 24,
wherein the code also encodes information specifying a normal pixel value range for the background area that is within the acceptable pixel value range for the background area, and the method further comprises:
causing the analysis unit to determine whether the background area optical density falls within the normal pixel value range for the background area, and
causing the analysis unit to output a warning indicator but not the error message when it is determined that the background area optical density falls within the acceptable pixel value range for the background area but not within the normal pixel value range for the background area.

26. An analyzing system, comprising:
a test piece that includes a reaction area, a background area, and a code area and that is configured to receive a specimen, the reaction area being configured to exhibit a reaction color when exposed to a test substance included in the received specimen, and the code area displaying a code that encodes information specifying the reaction color and an acceptable pixel value range for the background area; and
an analyzing apparatus that analyzes the test piece and that includes:
an image detection unit that images the reaction area, the background area, and the code area of the test piece,
a test piece receptacle configured to receive the test piece such that at least the reaction area, the background area, and the code area of the test piece are within a view field area of the image detection unit,
an analysis unit that:
detects the code in the image of the code area and decodes the code, thereby obtaining from the code the information specifying the reaction color and the acceptable pixel value range for the background area,
determine a concentration of the test substance in the specimen by determining a reaction area optical density from the image of the reaction area and comparing the reaction area optical density to calibration information corresponding to the reaction color specified by the information obtained from the code by the analysis unit, and
determine a background area optical density from the image of the background area and determine whether the background area optical density falls within the acceptable pixel value range for the background area; and
a display unit that displays analysis results,
wherein the analysis results include the determined concentration when the analysis unit determines that the background area optical density falls within the acceptable pixel value range for the background area.

27. An analyzing apparatus, comprising:
an image detection unit that detects images,
an analysis unit that analyzes the images detected by the image detection unit, such that, when the images are of a reaction area, a background area, and a code area of a test piece, the reaction area being configured to exhibit a reaction color when exposed to a predetermined test substance in a specimen and the code area displaying a code that encodes information specifying the reaction color and an acceptable pixel value range for the background area, the analysis unit:
  detects the code in the image of the code area,
  decodes the code,
  determines a reaction area optical density from the image of the reaction area and compares the reaction area optical density to calibration information corresponding to the reaction color, and
  determines a background area optical density from the image of the background area and determines whether the background area optical density falls within the acceptable pixel value range for the background area.

28. An analyzing apparatus, comprising:
a test piece receptacle configured to receive a test piece such that at least part of the test piece is within an imaging area;
an image detection unit that detect images of the imaging area;
an analysis unit configured to analyze the images detected by the image detection unit, such that, when the images are of a reaction area, a background area, and a code area of the test piece, the reaction area being configured to exhibit a reaction color when exposed to a predetermined test substance in a specimen and the code area displaying a code that encodes information specifying the reaction color and an acceptable pixel value range for the background area, the analysis unit:
  obtains the information specifying the reaction color and the acceptable pixel value range for the background area from the image of the code area by detecting the code in the image of the code area and decoding the code,
  calculates a concentration of the test substance in the specimen by determining a reaction area optical density from the image of the reaction area and comparing the reaction area optical density to calibration information corresponding to the reaction color, and
  determines whether a pixel value of a pixel in the image of the background area falls within the acceptable pixel value range for the background area;
a display unit that displays analysis results, wherein the analysis results include the determined concentration when the analysis unit determines that the background area optical density falls within the acceptable pixel value range for the background area; and
a control unit configured to control operations of the analyzing apparatus.

* * * * *